United States Patent

Lau et al.

[11] Patent Number: 5,834,166
[45] Date of Patent: Nov. 10, 1998

[54] PHOTOGRAPHIC ELEMENT CONTAINING A PARTICULAR CYAN DYE-FORMING COUPLER

[75] Inventors: Philip T.S. Lau; Stanley W. Cowan; David Hoke, all of Rochester, N.Y.

[73] Assignee: Eastman Kodak Company, Rochester, N.Y.

[21] Appl. No.: 742,791

[22] Filed: Oct. 31, 1996

[51] Int. Cl.$^6$ ............................................. G03C 7/46
[52] U.S. Cl. ........................ 430/385; 430/553; 430/543
[58] Field of Search ................................. 430/552, 553, 430/543, 305, 383

[56] References Cited

U.S. PATENT DOCUMENTS 5,585,230  12/1996  Zengerle et al. ........................ 430/552

FOREIGN PATENT DOCUMENTS 0271323  6/1988  European Pat. Off. .

*Primary Examiner*—Geraldine Letscher
*Attorney, Agent, or Firm*—Arthur E. Kluegel

[57] ABSTRACT

The invention provides a photographic element which comprises a light-sensitive silver halide emulsion layer having associated therewith a cyan dye-forming coupler having the formula:

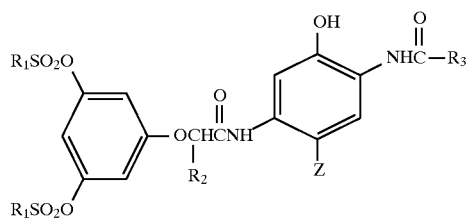

wherein:
  each $R_1$ independently represents an alkyl or aryl group;
  $R_2$ represents a linear or branched alkyl group of 1 to 20 carbon atoms;
  $R_3$ is selected from the group consisting of an alkyl group, an aryl group, a perfluoroalkyl group, or an arylamino group; and
  Z represents a hydrogen atom or a group capable of being split off by oxidized color developer.

The element of the invention exhibits improved cyan dye light stability.

21 Claims, No Drawings

PHOTOGRAPHIC ELEMENT CONTAINING A PARTICULAR CYAN DYE-FORMING COUPLER

FIELD OF THE INVENTION

The present invention relates to a photographic element comprising at least one red-sensitive layer which contains a silver halide emulsion and at least one 2,5-disubstituted phenolic cyan coupler having particular substituent groups.

BACKGROUND OF THE INVENTION

In recent years, a great deal of study has been conducted to improve dye-forming couplers for silver halide photosensitive materials in terms of improved image dye stability. However, an entirely satisfactory improvement has not yet been made, particularly in the area of cyan couplers.

The couplers commonly used to form cyan image dyes in color films and papers are generally of three types: amides of 1-hydroxy-2-naphtholic acid as represented by formula (I) and described in U.S. Pat. Nos. 2,313,138, 4,208,210, 5,283,163, 5,380,638, 5,476,757, and 5,457,020; 2-acylaminophenols as described by formula (II) and described in U.S. Pat. Nos. 2,367,531, 2,369,929, 2,423,730, 2,801,171, 3,772,002, 3,998,642, and 4,560,630; and 2,5-diacylaminophenols as described by formula (III) and described in U.S. Pat. Nos. 2,369,929, 2,895,826, 3,466,622, 3,758,308, 3,864,366, 3,880,661, 3,996,253, and 4,333,999. These types of couplers can be used either by being incorporated in the photographic silver halide emulsion layers or externally in the processing baths. In the former case the couplers must have ballast substituents built into the molecule to prevent the couplers from migrating from one layer into another.

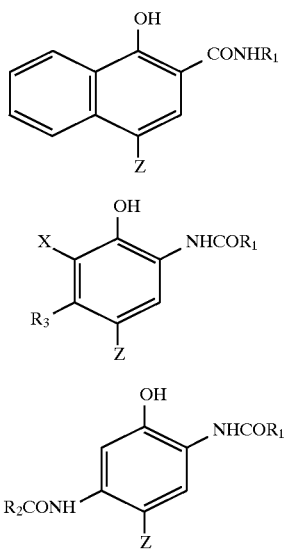

In each of the formulas (I), (II) and (III), $R_1$ represents an alkyl, aryl or arylamino substituent and Z represents a hydrogen atom or a group which is split off during the coupling reaction ("coupling-off group"). In (II), $R_3$ represents an alkyl group, usually methyl or ethyl, and X represents a halogen atom, usually chlorine or fluorine. In (III), $R_2$ represents an alkyl or aryl substituent, usually an alkyl group substituted at the alpha position by an aryloxy group.

Although these couplers have been used extensively in color photographic film and paper products, the dyes derived from each of the three types suffer from various deficiencies that make them not entirely satisfactory for use in color photographic papers.

Couplers of formula (I) yield image dyes that have poor stability to heat, humidity, light, and ferrous ions that are present in the bleaching solution. Furthermore, the absorption spectra of their image dyes are too bathochromically shifted (that is, shifted too far toward the long wavelength portion of the spectrum) to be useful in color photographic paper, and the dyes have an unacceptable side absorption in the short wavelength portion of the spectrum.

Cyan couplers of the 2-acylaminophenol type (II) have been widely employed in color photographic papers. Even though their dyes have excellent stability to light, they suffer from insufficient stability to heat and humidity to meet the more stringent requirements of modem products; furthermore, as with the couplers of formula I, the image dyes have an unacceptable side absorption in the short wavelength portion of the spectrum.

The image dyes derived from heretofore disclosed couplers of the 2,5-diacylaminophenol type (III) have excellent stability to heat and humidity, but they have poor stability to light which render them unsuitable for use in color papers.

Couplers are normally incorporated into photographic elements by first dissolving them in one or a combination of high-boiling organic solvents (often known in the art, and referred to herein, as "coupler solvents"), then dispersing the resulting solution into a mixture of gelatin, water, and a suitable surfactant, using any of several means of emulsification.

Many types of coupler solvents are known to the photographic art. These include a variety of esters, amides, phosphate esters, alcohols, phenols, and others. The most commonly used coupler solvents are phosphate esters such as tricresyl phosphate and tris-(2-ethylhexyl phosphate) and phthalates such as n-butyl phthalate and isodecyl phthalate. In the commercial photographic trade, phthalates are used almost exclusively with cyan couplers. Other examples of coupler solvents are found in U.S. Pat. No. 4,827,019 and references cited therein.

There has been a need to provide a photographic element which does not have the inherent disadvantages of the known couplers. Accordingly, it is a problem to be solved to provide a photographic element which not only exhibits satisfactory photographic properties such as coupling efficiency and dye hue, but which also yields a cyan dye which exhibits excellent stability, particularly to light.

SUMMARY OF THE INVENTION

The invention provides a photographic element which comprises a light-sensitive silver halide emulsion layer having associated therewith a cyan dye-forming coupler having the formula:

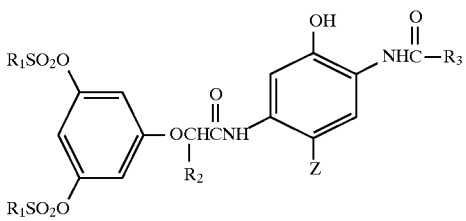

wherein:
each $R_1$ independently represents an alkyl or aryl group;
$R_2$ represents a linear or branched alkyl group of 1 to 20 carbon atoms;

$R_3$ is selected from the group consisting of an alkyl group, an aryl group, a perfluoroalkyl group, or an arylamino group; and Z represents a hydrogen atom or a group capable of being split off by oxidized color developer.

The invention also encompasses the advantageous coupler, the element on a reflective support, and a process for forming an image in the element of the invention.

DETAILED DESCRIPTION OF THE INVENTION

The invention is generally described in the Summary of the Invention with reference to the formula:

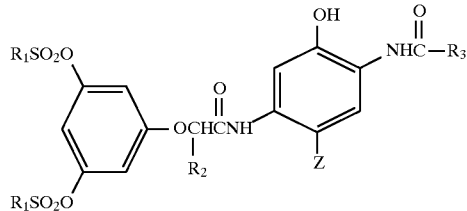

In the formula, each $R_1$ independently represents an alkyl group (linear or branched, saturated or unsaturated) having preferably 1 to 20 carbon atoms, such as methyl, isopropyl, butyl, or dodecyl, or an aryl group having preferably 6–30 carbon atoms, which may be optionally substituted by, for example, 1 to 5 halogen atoms, a cyano group, a carbonyl group, a carbonamido group, a sulfonamido group, a carboxy group, a sulfo group, an alkyl group, an aryl group, an alkoxy group, an aryloxy group, an alkylthio group, an arylthio group, an alkylsulfonyl group or an arylsulfonyl group.

$R_2$ represents a linear or branched alkyl group of 1 to 20 carbon atoms and conveniently an alkyl group of up to 4 carbon atoms.

$R_3$ represents an alkyl group (linear or branched, saturated or unsaturated) having preferably 1 to 20 carbon atoms, such as methyl, propyl or dodecyl, including a perfluoroalkyl group, such as trifluoromethyl or perfluorotetradecyl, the alkyl groups more preferably having 3 to 8 carbon atoms, such as heptafluoropropyl or heptadecafluorooctyl; an aryl group having preferably 6 to 30 carbon atoms; or an arylamino group having preferably 6 to 30 carbon atoms. If $R_3$ is an aryl group or an arylamino group it may be substituted by 1 to 5 groups independently selected from, for example, a halogen atom, a cyano group, a carbonyl group, a carbonamido group, a sulfonamido group, a carboxy group, a sulfo group, an alkyl group, an aryl group, an alkoxy group, an aryloxy group, an alkylthio group, an arylthio group, an alkylsulfonyl group or an arylsulfonyl group.

In the formula, Z represents a hydrogen atom or a group which can be split off by the reaction of the coupler with an oxidized color developing agent, known in the art as a "coupling-off group." Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction, and the like.

The presence of hydrogen at the coupling site (the site on the coupler molecule at which Z is attached) provides a 4-equivalent coupler, and the presence of a coupling-off group other than hydrogen usually provides a 2-equivalent coupler. Representative classes of such coupling-off groups include, for example, halogen, alkoxy, aryloxy, heterocyclyloxy, sulfonyloxy, acyloxy, acyl, heterocyclyl, sulfonamido, heterocyclylthio, benzothiazolyl, phosophonyloxy, alkylthio, arylthio, and arylazo. These coupling-off groups are described in the art, for example, in U.S. Pat. Nos. 2,455,169, 3,227,551, 3,432,521, 3,467,563, 3,617,291, 3,880,661, 4,052,212, and 4,134,766; and in U. K. Patents and published applications 1,466,728, 1,531,927, 1,533,039, 2,066,755A, and 2,017,704A, the disclosures of which are incorporated herein by reference. Halogen, alkoxy and aryloxy groups are most suitable.

It is essential that the substituent groups $R_1$, $R_2$, and $R_3$ in the formula be selected so as to adequately ballast the coupler and the resulting dye in the organic solvent in which the coupler is dispersed. The ballasting may be accomplished by providing hydrophobic substituent groups in one or more of the substituent groups $R_1$, $R_2$, and $R_3$. Generally, a ballast group is an organic radical of such size and configuration as to confer on the coupler molecule sufficient bulk and aqueous insolubility as to render the coupler substantially nondiffusible from the layer in which it is coated in a photographic element. Thus the combination of substituent groups $R_1$, $R_2$, and $R_3$ in the formula are suitably chosen to meet these criteria. To be effective, the ballast typically contains 10 to 30 aliphatic carbon atoms, and may be suitably located in one or more of substituents $R_1$, $R_2$, and $R_3$. Accordingly, suitable ballasting may also be accomplished by providing a plurality of groups which in combination meet these criteria.

The following examples further illustrate the couplers of the invention. It is not to be construed that the present invention is limited to these examples.

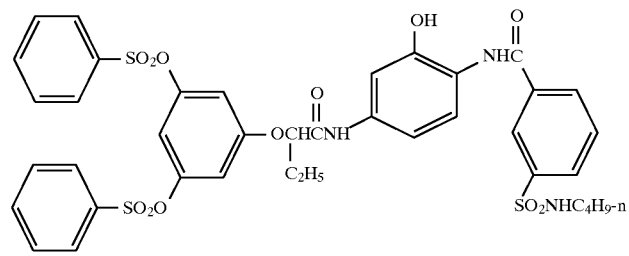

C-1

-continued
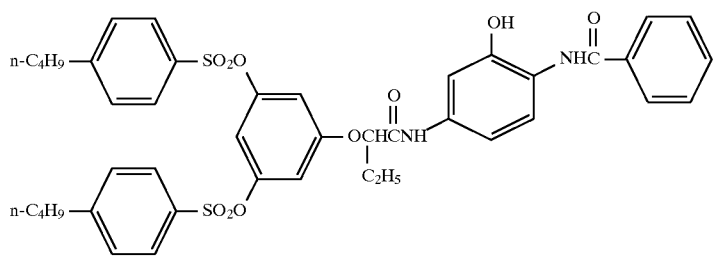
C-2
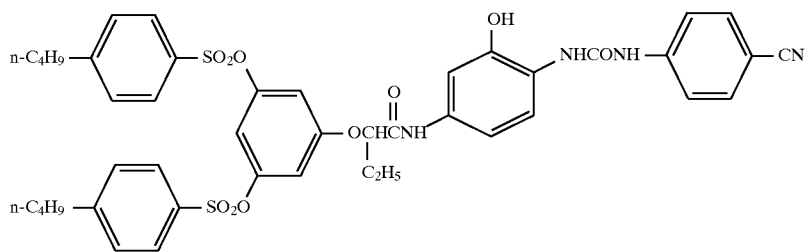
C-3
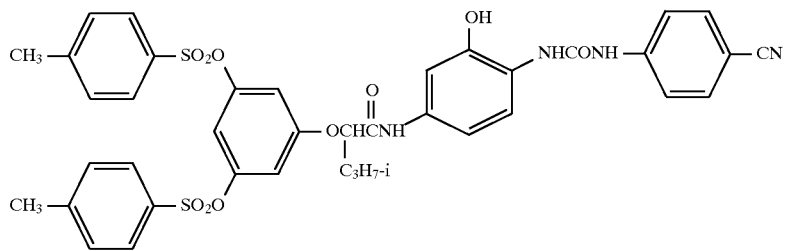
C-4
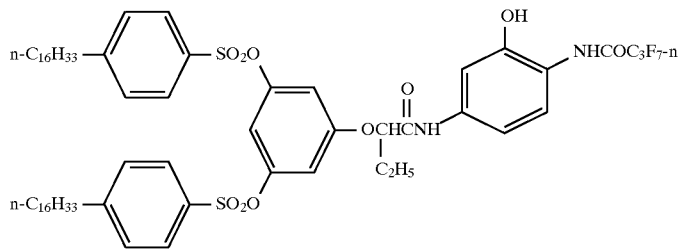
C-5
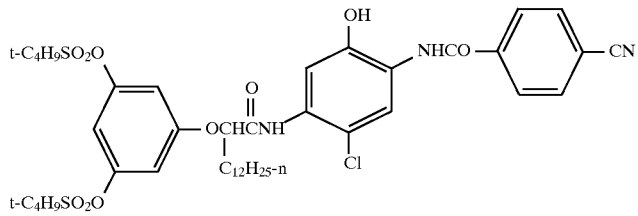
C-6
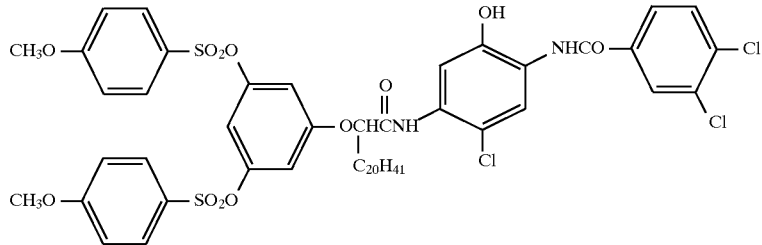
C-7

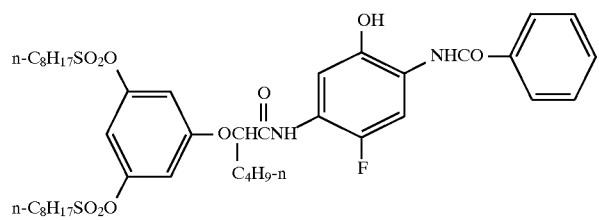
C-8
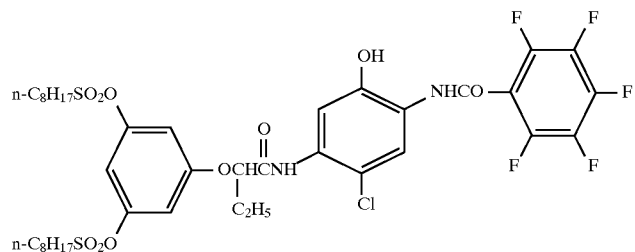
C-9
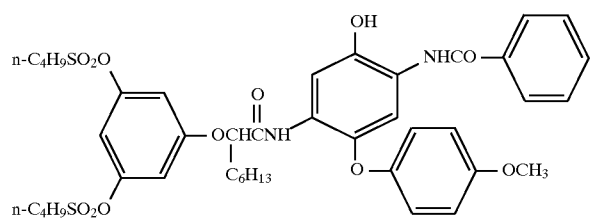
C-10
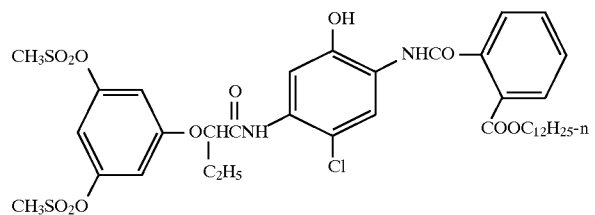
C-11
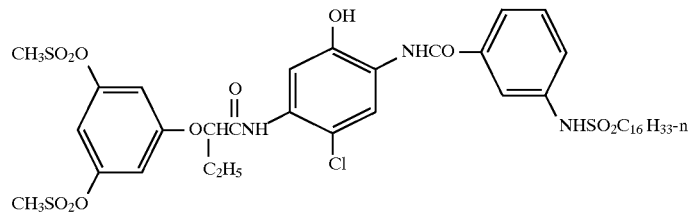
C-12
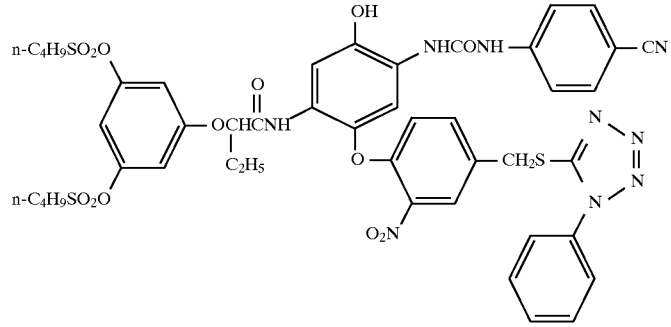
C-13

-continued
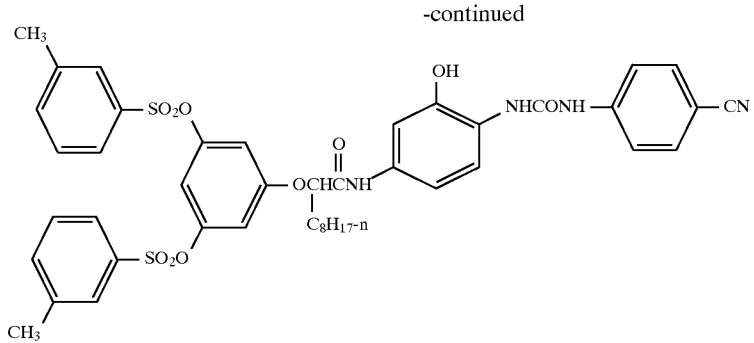
C-14
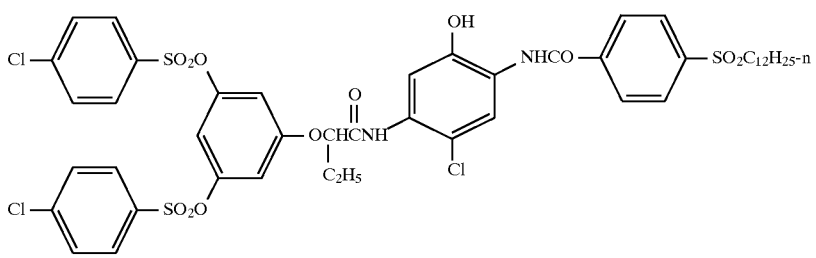
C-15
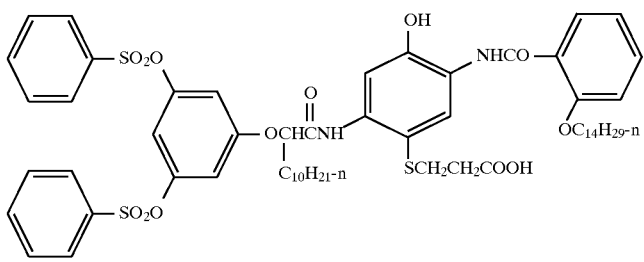
C-16
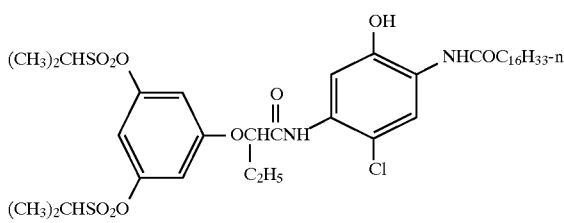
C-17
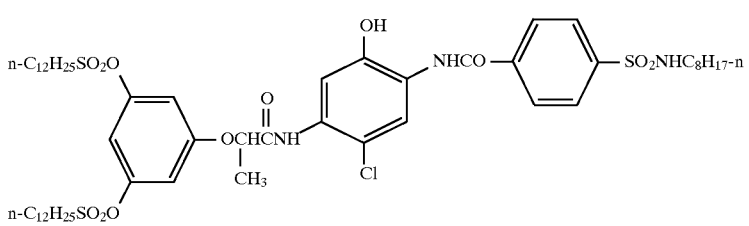
C-18
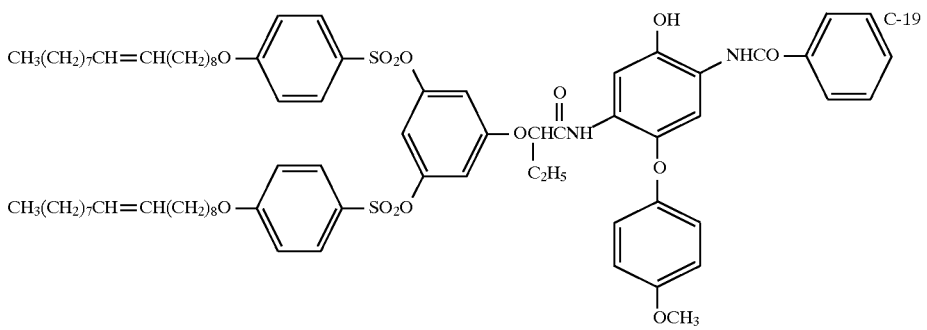
C-19
Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control migration, it may be desirable to include a high molecular weight hydrophobe or "ballast" group in non-invention coupler molecules. Representative ballast groups include substituted or unsubstituted alkyl or aryl groups containing 8 to 48 carbon atoms. Representative substituents on such groups include alkyl, aryl, alkoxy, aryloxy, alhylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1994, Item 36544, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Coupling-off groups are well known in the art as explained earlier. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006,755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895,826, 3,002,836, 3,034,892, 3,041,236, 4,333,999, 4,883,746 and "Farbkuppler-eine Literature Ubersicht," published in Agfa Mitteilungen, Band III, pp. 156–175 (1961). Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine Literature Ubersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: UK. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3- position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859, 578; U.S. Pat. No. 4,912,025); antifogging and anti colormixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543, 323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148, 062; 3,227,554; 3,384,657; 3,379,529; 3,615,506; 3,617, 291; 3,620,746; 3,701,783; 3,733,201; 4,049,455; 4,095, 984; 4,126,459; 4,149,886; 4,150,228; 4,211,562; 4,248, 962; 4,259,437; 4,362,878; 4,409,323; 4,477,563; 4,782, 012; 4,962,018; 4,500,634; 4,579,816; 4,607,004; 4,618, 571; 4,678,739; 4,746,600; 4,746,601; 4,791,049; 4,857, 447; 4,865,959; 4,880,342; 4,886,736; 4,937,179; 4,946, 767; 4,948,716; 4,952,485; 4,956,269; 4,959,299; 4,966, 835; 4,985,336 as well as in patent publications GB 1,560, 240; GB 2,007,662; GB 2,032,914; GB 2,099,167; DE 2,842,063, DE 2,937,127; DE 3,636,824; DE 3,644,416 as well as the following European Patent Publications: 272, 573; 335,319; 336,411; 346, 899; 362, 870; 365,252; 365, 346; 373,382; 376,212; 377,463; 378,236; 384,670; 396, 486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

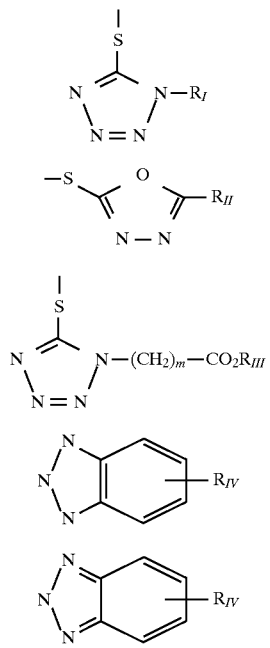

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

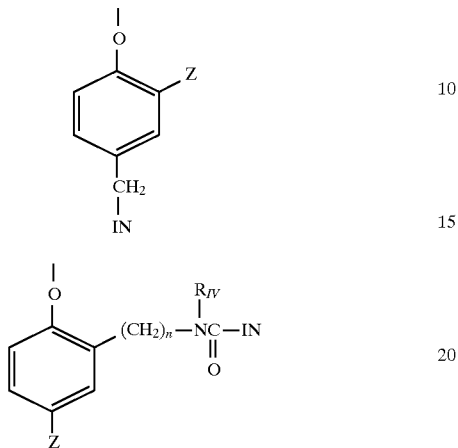

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

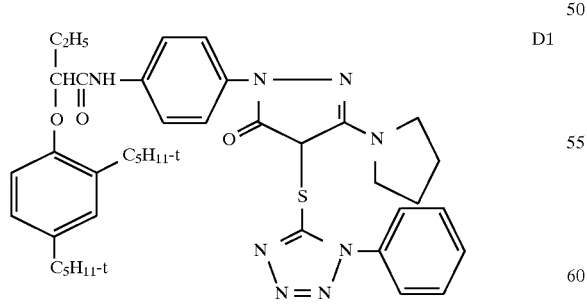

D1

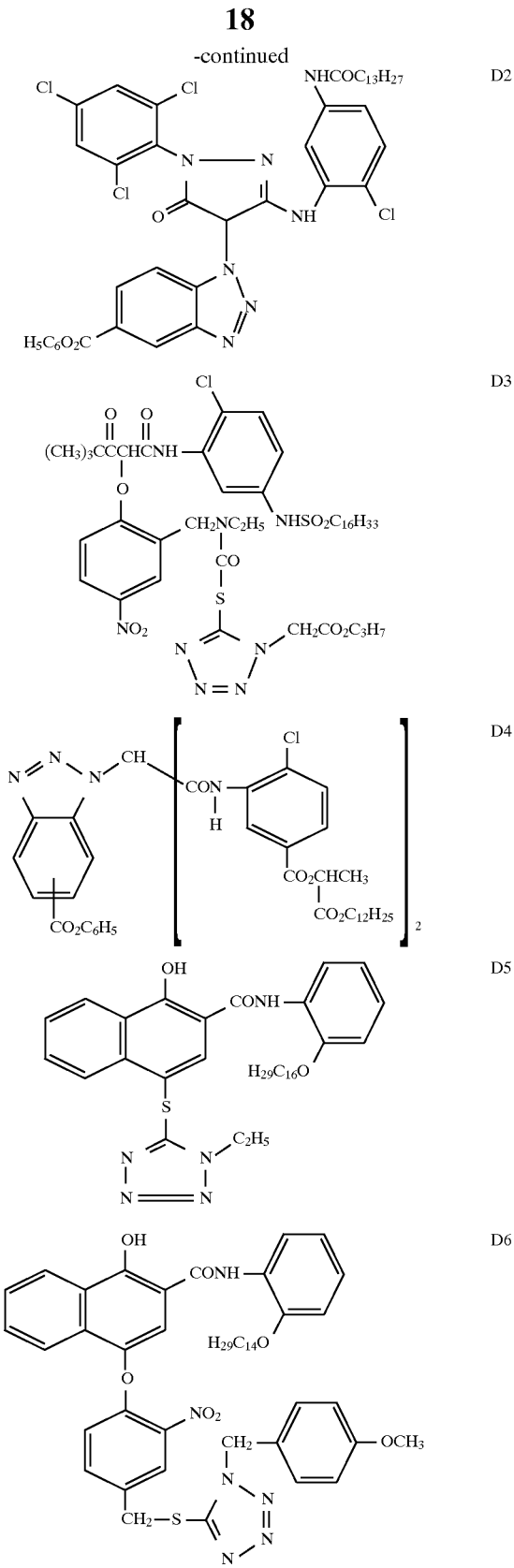

-continued

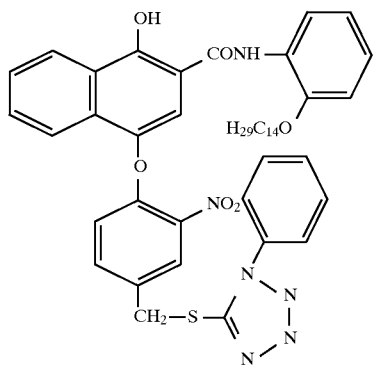
D7

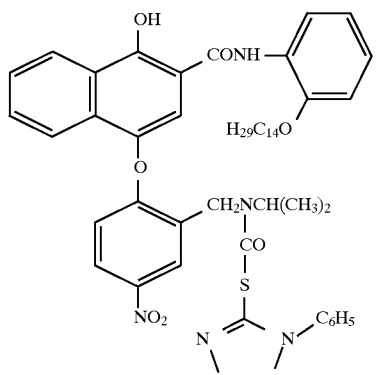
D8

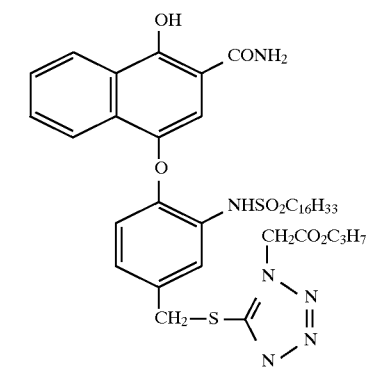
D9

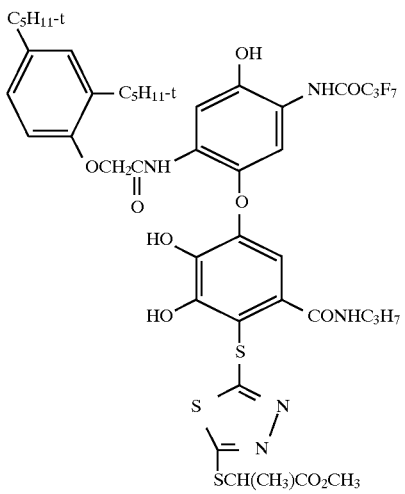
D-10

-continued

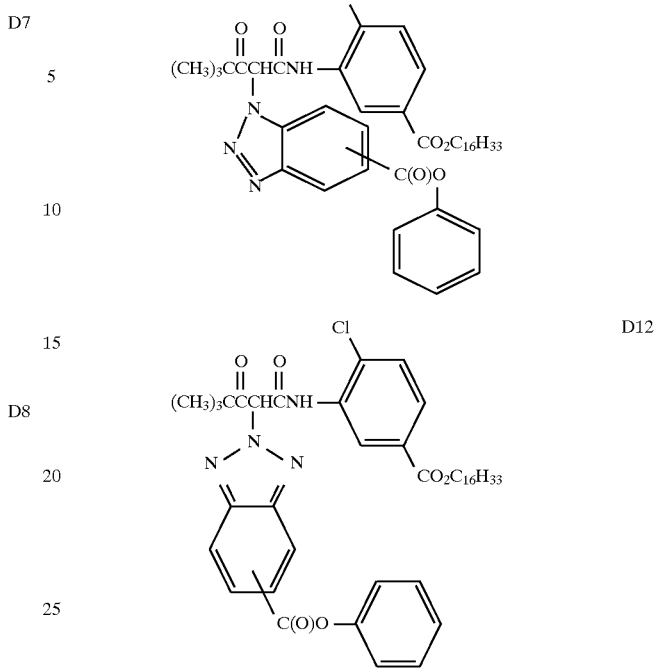

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.07 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. One type of such element is designed for image capture and speed (the sensitivity of the element to low light conditions) is often critical to obtaining sufficient image in such elements. When such elements are to be used to generate a color print, they are typically processed in known color negative processes such as the Kodak C-41 process as described in The British Journal of Photography Annual of 1988, pages 191–198. If such an element is to be employed to generate a viewable projection print as for a motion picture, a process such as the Kodak ECN-2 process described in the H-24 Manual available from Eastman Kodak Co. may be employed. Color negative development times are typically 3'15" or less and preferably 90 or even 60 seconds or less.

Color reflection prints may be processed, for example, using the Kodak RA-4 process as described in The British Journal of Photography Annual of 1988, Pp 198–199; color projection prints may be processed, for example, in accordance with the Kodak ECP-2 process as described in the H-24 Manual. Color print development times are typically 90 seconds or less and preferably 45 or even 30 seconds or less.

To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process. Alternatively, a direct positive emulsion can be employed to obtain a positive image.

The above emulsions are typically sold with instructions to process using the appropriate method such as the mentioned Kodak C-41, Kodak RA-4, or Kodak E-6 process.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the patent applications, patents and other publications referred to in this specification are incorporated herein by reference.

SYNTHETIC EXAMPLES

The cyan couplers of this invention can be prepared by reacting alkyl or aryl acid chlorides with an appropriate aminophenol, such as 2-amino-5-nitrophenol, to form the 2-carbonamido coupler intermediate. The nitro group of the coupler intermediate can then be reduced and a separately prepared aryloxy-containing acid chloride ballast can be attached thereto by conventional procedures. The synthesis of cyan coupler C-2 will further illustrate the invention.

Preparation of the phenolic coupler intermediate

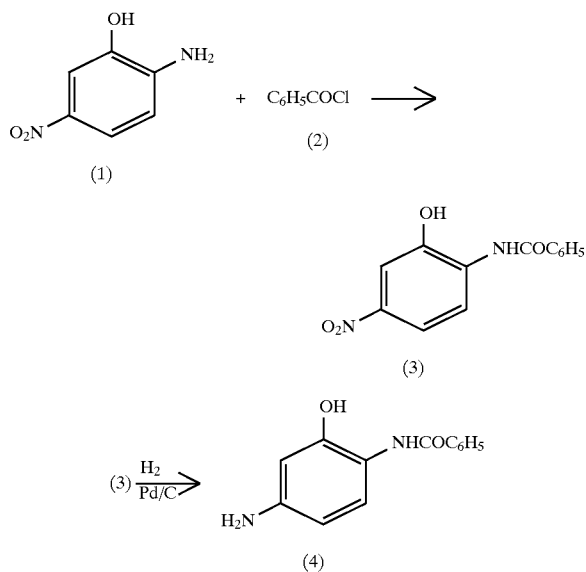

To a stirred solution of 30.8 g (0.20 mole) 2-amino-5-nitrophenol (1) and 45.8 g (0.40 mole) N,N-dimethylaniline in 500 ml THF was added 29.5 g (0.21 mole) benzoyl chloride (2). After stirring for 1.0 hour the mixture was drowned in ice water containing 15 ml conc. HCl. The solid that precipitated out was collected, washed with HO and recrystallized from acetonitrile to give 41.8 g (81%) of the nitro compound (3).

A solution of 3.1 g (0.012 mole) of (3) and 1.5 g 10% Pd/C was reduced at room temperature under 50 pounds per square inch of hydrogen for 3 hours. The catalyst was filtered off to give the reduced 2-benzamido-5-aminophenol (4) which was stored under a blanket of nitrogen while the aryloxy-containing acid chloride ballast was being prepared.

Preparation of acid chloride ballast

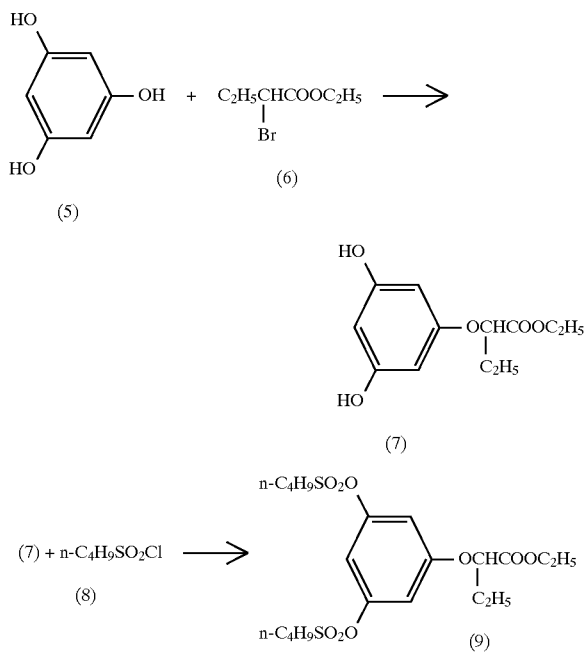

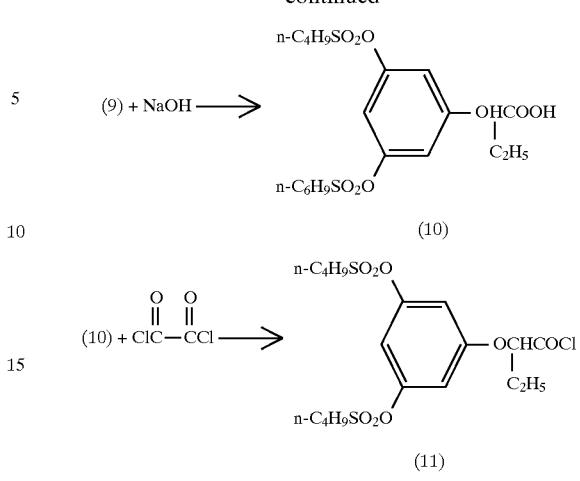

To a stirred solution of 75.7 g (0.60 mole) phloroglucinol (5 and 30 g (0.20 mole) ethyl α-bromobutyrate (6) in 200 ml DMF was added slowly 9.6 g (0.20 mole) 50% sodium hydride oil dispersion. After stirring overnight the mixture was poured into ice water containing 20 ml conc. HCl. The oil which separated was extracted with EtOAc, dried over $MgSO_4$ and the solvent removed under reduced pressure. The crude residue was taken up in $CH_2Cl_2$ and passed through a silica gel column, eluting with $CH_2Cl_2$-ether solvent mixture. The fractions containing the product were combined and the solvent removed to give 20 g white solid product (2).

To a stirred solution of 10.8 g (0.05 mole) ethyl (α-(3,5-dihydroxyphenoxy)butyrate (7) and 10.1 g (0.10 mole) triethylamine in 100 ml EtOAc was added in one portion 15.6 g (0.10 mole) butylsulfonyl chloride (8). After stirring for 2 hours at room temperature the mixture was transferred to a separatory funnel and washed 2× with 10% HCl. The EtOAc solution was dried over $MgSO_4$, the solvent was removed, the residual oil was taken up in $CH_2Cl$ and was passed through a short silica gel column, eluting with $CH_2Cl$. The fractions containing the product were combined and the solvent removed to give 16 g pure ballast acid (10 as a yellow oil.

To a stirred solution of 5.5 g (0.012 mole) ballast acid (10) in 100 ml $CH_2Cl$ was added at room temperature 3.1 g (0.024 mole) oxalyl chloride and 3–5 drops DMF. After stirring for 2 hours the excess oxalyl chloride and solvent were removed to give the desired ballast acid chloride (I).

Preparation of cyan coupler C-2

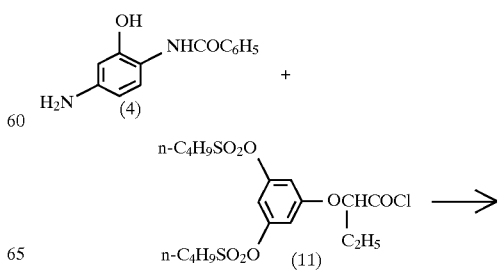

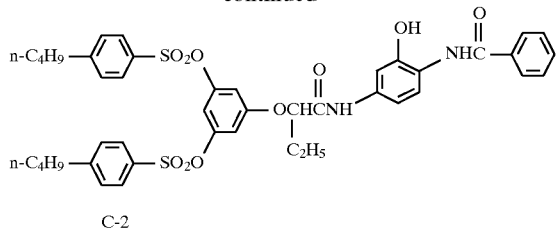

C-2

To a stirred solution of 2.7 g (0.012 mole) 2-benzamido-5-aminophenol (4) and 4.4 g (0.036 mole) N,N-dimethylaniline in 150 ml THF was added under a blanket of nitrogen 5.7 g (0.012 mole) ballast acid chloride (11) prepared above. After stirring at room temperature for 1.0 hour the mixture was poured into ice water containing 10 ml conc. HCl. The oil which separated was extracted with EtOAc, dried over MgSO$_4$, and the solvent removed to give a brown glassy solid. The solid was crystallized from toluene to give 6.3 g (79.2%) snow white product whose structure corresponds to cyan coupler C-2 of the invention, m.p. 105°–107° C.

Calc. for $C_{31}H_{38}N_2O_{10}S_2$ C, 56.2; H, 5.8; N, 4.2

Found: C, 56.6; H, 5.8; N, 4.1

Preparation of Photographic Elements

On a gel-subbed, polyethylene-coated paper support were coated the following layers:

First Layer

An underlayer containing 3.23 grams gelatin per square meter.

Second Layer

A photosensitive layer containing (per square meter) 2.15 grams gelatin, an amount of red-sensitized silver chloride emulsion containing the amount of silver indicated in Table 1; a dispersion containing $8.61 \times 10^{-4}$ mole of the coupler indicated in Table 1; and 0.043 gram surfactant Alkanol XC (trademark of E. I. Dupont Co.)(in addition to the Alkanol XC used to prepare the coupler dispersion). The coupler dispersion contained the coupler, all of the gelatin in the layer except that supplied by the emulsion, an amount of the coupler solvent indicated in Table equal to the weight of coupler, and 0.22 gram Alkanol XC.

Third Layer

A protective layer containing (per square meter) 1.40 grams gelatin, 0.15 gram bis(vinylsulfonyl)methane, 0.043 gram Alkanol XC, and $4.40 \times 10^{-6}$ gram tetraethylammonium perfluorooctanesulfonate.

The coupler solvents used were dibutyl phthalate (S-1) and p-dodecylphenol (S-2).

The following comparison couplers were used:

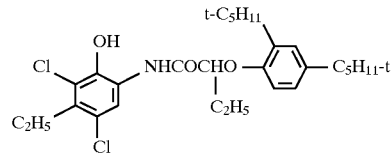

(CC-1)

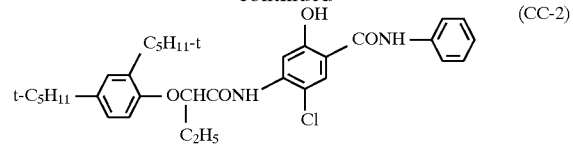

(CC-2)

Comparison coupler CC-1 is one that is used in many commercially available color photographic papers. Comparison coupler CC-2 is similar to the couplers of the invention but does not have the requisite ballast group.

Preparation of Processed Photographic Examples

Processed samples were prepared by exposing the coatings through a step wedge and processing as follows:

| Process Step | Time (min.) | Temp. (°C.) |
|---|---|---|
| Developer | 0.75 | 35.0 |
| Bleach-Fix | 0.75 | 35.0 |
| Water wash | 1.50 | 35.0 |

The processing solutions used in the above process had the following compositions (amounts per liter of solution):

| Developer | |
|---|---|
| Triethanolamine | 12.41 g |
| Blankophor REU (trademark of Mobay Corp.) | 2.30 g |
| Lithium polystyrene sulfonate | 0.09 g |
| N,N-Diethylhydroxylamine | 4.59 g |
| Lithium sulfate | 2.70 g |
| Developing agent Dev-1 | 5.00 g |
| 1-Hydroxyethyl-1,1-diphosphonic acid | 0.49 g |
| Potassium carbonate, anhydrous | 21.16 g |
| Potassium chloride | 1.60 g |
| Potassium bromide | 7.00 mg |
| pH adjusted to 10.4 at 26.7 C. | |
| Bleach-Fix | |
| Solution of ammonium thiosulfate | 71.85 g |
| Ammonium sulfite | 5.10 g |
| Sodium metabisulfite | 10.00 g |
| Acetic acid | 10.20 g |
| Ammonium ferric ethylenediaminetetra acetate | 48.58 g |
| Ethylenediaminetetraacetic acid | 3.86 g |
| pH adjusted to 6.7 at 26.7° C. | |

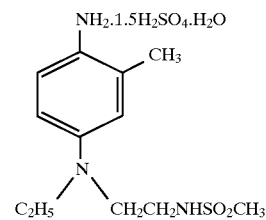

(Dev-1)

The density of each step of each strip was measured. The strips were then covered by UV absorbing filters (in lieu of coating a similar filter layer over the photosensitive layer of the photographic element) and subjected to irradiation by the light of a xenon arc lamp at an intensity of 50 klux for one week. The densities were 10 again measured. The stabilities of the dyes were calculated as the density remaining from an initial density of 1.0. The relative stabilities vs CC-1 ("Rel Stab") are shown in Table 1.

TABLE 1

| Invention or Comparison | Coupler | Solvent | g Ag per m² | Rel Stab |
|---|---|---|---|---|
| Comparison | CC-1 | S-1 | 0.19 | 1.00 |
| Comparison | CC-2 | S-1 | 0.19 | 0.89 |
| Invention | C-1 | S-1 | 0.39 | 1.01 |
| Invention | C-2 | S-2 | 0.39 | 1.08 |
| Invention | C-3 | S-1 | 0.39 | 1.12 |
| Invention | C-3 | S-2 | 0.39 | 1.14 |

The data in Table 1 show that the image dyes derived from the cyan couplers of the invention had light stabilities equal to or better than that of the dye from the comparison coupler CC-1 which is currently used in many color paper products, and significantly better than that of the dye from comparison coupler CC-2 which differs from the couplers of the invention only in the ballast.

What is claimed is:

1. A photographic element which comprises a light-sensitive silver halide emulsion layer having associated therewith a cyan dye-forming coupler having the formula:

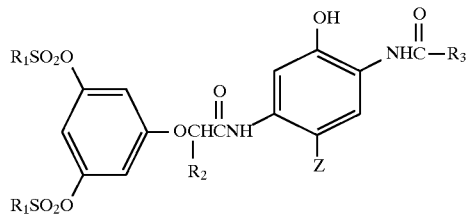

wherein:
each $R_1$ independently represents an alkyl or aryl group;
$R_2$ represents a linear or branched alkyl group of 1 to 20 carbon atoms;
$R_3$ is selected from the group consisting of an alkyl group, an aryl group, a perfluoroalkyl group, or an arylamino group; and
Z represents a hydrogen atom or a group capable of being split off by oxidized color developer.

2. The element of claim 1 wherein each $R_1$ independently represents a phenyl group.

3. The element of claim 2 wherein at least one of the phenyl groups is substituted.

4. The element of claim 3 wherein the phenyl group is substituted with an alkyl group.

5. The element of claim 1 wherein $R_3$ represents a phenyl group.

6. The element of claim 5 wherein $R_3$ represents a substituted phenyl group.

7. The element of claim 6 wherein $R_3$ represents a phenyl group substituted with a sulfamoyl group or an arylamino group.

8. The element of claim 7 wherein $R_3$ represents an anilino group.

9. The element of claim 1 wherein $R_1$ is an alkyl group of up to 4 carbon atoms.

10. The element of claim 1 wherein the cyan coupler has the formula:

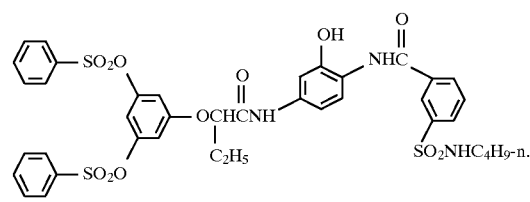

11. The element of claim 1 wherein the cyan coupler has the formula:

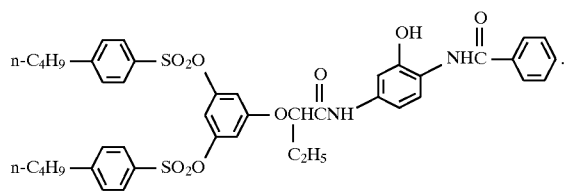

12. The element of claim 1 wherein the cyan coupler has the formula:

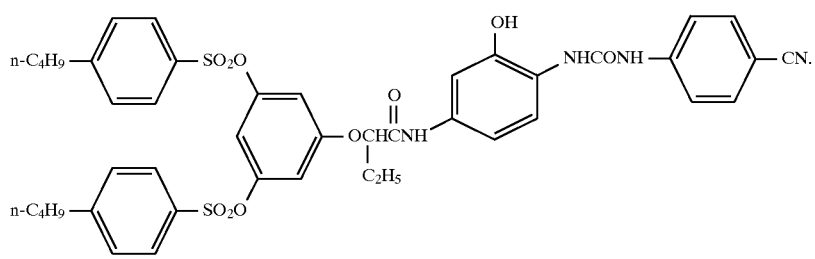

13. A photographic silver halide emulsion layer sensitized to red light comprising a cyan dye-forming coupler having the formula:

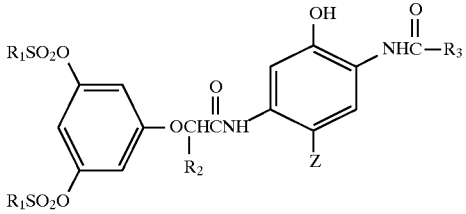

wherein:
each $R_1$ independently represents an alkyl or aryl group;
$R_2$ represents a linear or branched alkyl group of 1 to 20 carbon atoms;

R₃ is selected from the group consisting of an alkyl group, an aryl group, a perfluoroalkyl group, or an arylamino group; and Z represents a hydrogen atom or a group capable of being split off by oxidized color developer.

14. A multicolor photographic element comprising a silver halide emulsion layer sensitized to blue light, a silver halide emulsion layer sensitized to green light, and a silver halide emulsion layer sensitized to red light, wherein the layer sensitized to red light has associated therewith a cyan dye-forming coupler having the formula:

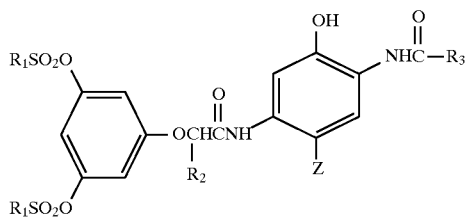

wherein:

each R₁ independently represents an alkyl or aryl group;

R₂ represents a linear or branched alkyl group of 1 to 20 carbon atoms;

R₃ is selected from the group consisting of an alkyl group, an aryl group, a perfluoroalkyl group, or an arylamino group; and Z represents a hydrogen atom or a group capable of being split off by oxidized color developer.

15. A multicolor photographic element comprising on a reflective support a silver halide emulsion layer sensitized to blue light, a silver halide emulsion layer sensitized to green light, and a silver halide emulsion layer sensitized to red light, wherein the layer sensitized to red light has associated therewith a cyan dye-forming coupler having the formula:

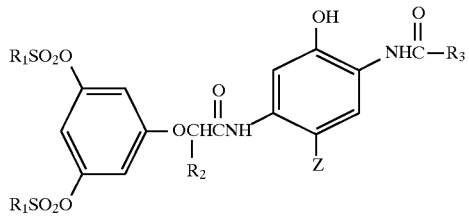

wherein:

each R₁ independently represents an alkyl or aryl group;

R₂ represents a linear or branched alkyl group of 1 to 20 carbon atoms;

R₃ is selected from the group consisting of an alkyl group, an aryl group, a perfluoroalkyl group, or an arylamino group; and Z represents a hydrogen atom or a group capable of being split off by oxidized color developer.

16. A cyan dye-forming coupler having the formula:

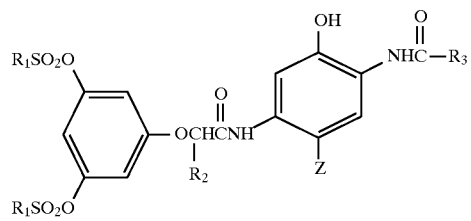

wherein:

each R₁ independently represents an alkyl or aryl group;

R₂ represents a linear or branched alkyl group of 1 to 20 carbon atoms;

R₃ is selected from the group consisting of an alkyl group, an aryl group, a perfluoroalkyl group, or an arylamino group; and Z represents a hydrogen atom or a group capable of being split off by oxidized color developer.

17. A process of forming an image in the element of claim 1 after the same has been exposed to light comprising contacting the element with a color developing agent.

18. The process of claim 17 wherein the color developing agent is a p-phenylenediamine.

19. The process of claim 17 wherein the development step is performed in 90 seconds or less.

20. The process of claim 19 wherein the development step is performed in 60 seconds or less.

21. The process of claim 20 wherein the development step is performed in 45 seconds or less.

* * * * *